US007211441B2

(12) United States Patent
Dobretsov et al.

(10) Patent No.: US 7,211,441 B2
(45) Date of Patent: May 1, 2007

(54) LIPOPROTEIN ASSAY

(75) Inventors: Gennady Evgenievich Dobretsov, Moscow (RU); Tatiana Ivanovna Syrejshchikova, Moscow (RU); Nikolay Konstantinovich Kurek, Moscow (RU); David Clarke, Warrington (GB); Gareth Jones, Warrington (GB); Mikhail Nikolaevich Yakimenko, deceased, late of Moscow (RU); by Olga Polyannikova, legal representative, Moscow (RU); Boris Mordukhovich Krasovitsky, Kharkov (UA)

(73) Assignee: Council for the Central Laboratory of the Research Councils, Daresbury, Warrington (GB)

( * ) Notice: Subject to any disclaimer, the term of this patent is extended or adjusted under 35 U.S.C. 154(b) by 576 days.

(21) Appl. No.: 10/181,365

(22) PCT Filed: Jan. 17, 2001

(86) PCT No.: PCT/GB01/00167

§ 371 (c)(1),
(2), (4) Date: Oct. 23, 2002

(87) PCT Pub. No.: WO01/53829

PCT Pub. Date: Jul. 26, 2001

(65) Prior Publication Data

US 2003/0101004 A1    May 29, 2003

(30) Foreign Application Priority Data

Jan. 18, 2000    (GB) ................................. 0001089.2

(51) Int. Cl.
*G01N 21/76* (2006.01)
(52) U.S. Cl. ........................ 436/172; 436/71; 436/800; 436/546; 435/973
(58) Field of Classification Search ................ 435/6, 435/7.1, 7.92, 973; 436/501, 518, 165, 172, 436/546, 800, 71
See application file for complete search history.

(56) References Cited

U.S. PATENT DOCUMENTS

| 4,877,746 | A  | * | 10/1989 | Jansson et al. ............. 436/518 |
| 6,309,888 | B1 | * | 10/2001 | Holvoet et al. ............... 436/71 |
| 6,383,819 | B1 | * |  5/2002 | Watanabe et al. ........... 436/518 |
| 6,727,102 | B1 | * |  4/2004 | Holvoet et al. ............. 436/501 |

FOREIGN PATENT DOCUMENTS

| EP | 0103558 A2 | 3/1984 |
| JP | 10332594 | 12/1998 |
| SU | 1476384 A1 | 4/1989 |
| SU | 1457386 A1 | 10/1992 |
| WO | WO 89/04375 | 5/1989 |
| WO | WO 91/06011 | 5/1991 |
| WO | WO 92/12255 | 7/1992 |
| WO | WO 88/07670 | 10/1998 |

OTHER PUBLICATIONS

Lapshin et al., Application of Fluorescent Probes in Medical Diagnosis, Sov. Med. Rev. B. Physiocochemical, vol. 3, pp. 37-101.*
Database WPI, Section Ch, Week 199323, Derwent Publications, Ltd., London, GB; AN 1993-186834, XP002165393 & SU 1 545 527 A (Krasovitskii B M), Jul. 23, 1992.
Database WPI, Section Ch, Week 199339, Derwent Publications, Ltd., London, GB; AN 1993-309983, XP002165394 & SU 1 457 386 A (Krasovitskii B M), Oct. 30, 1992.
Database WPI, Section Ch, Week 198235, Derwent Publications Ltd., London, GB; AN 1982-74280E, XP002165395 & SU 877 437 A (Mosc Med Inst), Oct. 30, 1981.
Database WPI, Section Ch, Week 199228, Derwent Publications Ltd., London, GB; AN 1992-232285, XP002165396 & SU 1 681 266 A (Phys Chem Medicine Res Inst), Sep. 30, 1991.
Database WPI, Section Ch, Week 199306, Derwent Publications, Ltd., London, GB; AN 1993-052004, XP 002165397 & SU 1 720 004 A (Health Min Phys Chem Res Inst), Mar. 15, 1992.
Gryzunov, Yu, et al: "Serum albumin binding sites properties in donors and in schizophrenia patients: the study of fluorescence decay of the probe K-35 using S-60 synchrotron pulse excitation" $12^{TH}$ National Synchrotron Radiation Conference, Novosibirsk, Russia, Jul. 14-18, 1998, vol. 448, No. 1-2—Jul. 1998, pp. 478-482, XP004206580, Nuclear Instruments & Methods in Physics Research, Section A (Accelerators, Spectrometers, Detectors and Associated Equipment), Jun. 21, 2000, Elsevier, Netherlands, ISSN: 0168-9002, p. 478.
Dobretsov, G. E., et al.,: "Time-resolved spectroscopy of the probe fluorescence in the study of human blood protein dynamic structure on SR beam" $12^{TH}$ National Synchrotron Radiation Conference, Novosibirsk, Russia, Jul. 14-18, 1998, vol. 448, No. 1-2,—Jul. 1998, pp. 471-477, XP004206579 Nuclear Instruments & Methods in Physics Research, Section A (Accelerators, Spectrometers, Detectors and Associated Equipment), Jun. 21, 2000, Elsevier, Netherlands, ISSN: 0168-9002, p. 471.
Dem'Yanov, G. V., et al.: "Observation of fluorescence anisotrophy decay for a lipid probe in artificial membranes" Kratkie Soobshcheniya PO Fizike, 1995, Allerton Press, Russia, No. 11-12—1995 pp. 15-19, XP000995214, p. 16.

(Continued)

Primary Examiner—Long V. Le
Assistant Examiner—Gary W. Counts
(74) Attorney, Agent, or Firm—Woodard, Emhardt, Moriarty, McNett & Henry LLP

(57) ABSTRACT

A method of assaying to determine the identity and/or concentration or relative concentration in a sample solution of a particular one of a number of different target molecule types, comprise the steps of: i) adding to the sample a probe substance which binds to the or each target molecule type and which when so bound fluoresces under appropriate excitation; ii) performing a time-resolved fluorescence measurement on the sample; and iii) making said determination from analysis of the time decay data obtained from said time-resolved fluorescence measurement.

10 Claims, 2 Drawing Sheets

OTHER PUBLICATIONS

Demyanov, G. V., et al.: "Characteristics of molecular fluorescence of a lipid probe in human blood lipoproteins exposed to synchrotron radiation" 10$^{TH}$ National Synchrotron Radiation Conference (SR '94), Novosibirsk, Russia, Jul. 11-15, 1994, vol. 359, No. 1-2, Jul. 11-15, 1994, pp. 342-344, XP000995488 Nuclear Instruments & Methods in Physics Research, Section A (Accelerators, Spectrometers, Detectors and Associated Equipment), May 1, 1995, Netherlands, ISSN: 0168-9002, p 342.

Demyanov, G. V., et al.: "Protein fluorescence decay of human serum with a very low density of lipoproteins exposed to synchrotron radiation" Ninth USSR National Conference on Synchrotron Radiation, Utilization, Moscow, USSR, Jun. 26-29, 1990, vol. A308, No. 1-2, pp. 215-218, XP000995480, Nuclear Instruments & Methods in Physics Research, Section A (Accelerators, Spectrometers, Detectors and Associated Equipment), Oct. 10, 1991, Netherlands, ISSN: 0168-9002, p. 215.

Kurek, N. K., et al.: "The use of synchrotron radiation to investigate the localization of fluorescent probes in model lipoproteins" Eighth USSR National Conference on Synchrotron Radiation Utilization, Novosibirsk, USSR, Aug. 18-22, 1988, vol. A282, No. 2-3, pp. 490-492, XP000995208, Nuclear Instruments & Methods in Physics Research, Section A (Accelerators, Spectrometers, Detectors and Associated Equipment), Oct. 10, 1989, Netherlands, ISSN: 0168-9002, p. 490.

You, Wendy W., et al: "3-(4-carboxybenzoyl)quinoline-2-carboxaldehyde, a reagent with broad dynamic range for the assay of proteins and lipoproteins in solution." Analytical Biochemistry, vol. 244, No. 2, 1997, pp. 277-282, XP000985955, ISSN: 003-2697, p. 277.

Harri Hakala, Pasi Virta, Harri Salo and Harri Lonnberg, Simultaneous detection of several oligonucleotides by time-resolved fluorometry: the use of a mixture of categorized microparticles in a sandwich type mixed-phase hybridization assay, *Nucleic Acids Research*, 1998, vol. 26, No. 24, Oxford University Press, pp. 5581-5588.

Eleftherios P. Diamandis, Robert C. Morton, Esther Reichestein, and Mohammad J. Khosravi, Multiple Fluorescence Labeling with Europium Chelators, Application to Time-Resolved Fluoroimmunoassays, *Analytical Chemistry*, vol. 61, No. 1, Jan. 1, 1989, pp. 48-53.

Tilley, Leann; Sawyer, William H.; Morrison, John R.; Fidge, Noel H., "Rotational Diffusion of Human Lipoproteins and Their Receptors as Determined by Time-resolved Phosphorescence Anistropy," *The Journal of Biological Chemistry*, Nov. 25, 1988, pp. 17541-17547, vol. 263, No. 33.

* cited by examiner

LIPOPROTEIN ASSAY

FIELD OF THE INVENTION

The present invention relates to a method of assaying to determine the identity and/or concentration or relative concentration in a sample solution of a particular one of a number of different target molecule types.

Particularly, but not exclusively, the invention relates to an assay for determining the identity of particular lipoproteins in protein mixtures, and in particular for discriminating between different classes of lipoprotein in a protein mixture such as blood plasma or serum.

BACKGROUND OF THE INVENTION

Lipoproteins, which are carriers of lipids, cholesterol and triglycerides, are amongst the major components of blood plasma or serum (for brevity hereinafter the term "plasma" will be used but references to "plasma" should be interpreted as references to plasma or serum). The lipoproteins found in blood plasma fall into three main classifications: high density lipoproteins (HDL), low density lipoproteins (LDL) and very low density lipoproteins (VLDL). It is well known that there is a strong relationship between the concentration of lipoproteins in blood plasma and the risk of atherosclerosis (i.e. cardio-vascular desease development). It is also known that the different classes of lipoproteins each play a different role in atherosclerosis. For instance, HDL is regarded as antiatherogenic whereas LDL is known to be highly atherogenic (the cholesterol it carries correlating closely with atherocloses development). VLDL is considered to be slightly atherogenic and of more significance in females.

Blood plasma is a complex mixture of a variety of proteins and although methods for separating and directly measuring the concentration of different classes of lipoproteins are known, such methods are complex and expensive. Accordingly, the conventional method of lipoprotein assay widely used in clinical laboratories is an indirect method in which the important LDL concentration is calculated from the measurement of total cholesterol concentration, triglyceride concentration and HDL concentration using the Fridedewald equation:

(CH-LDL)=CH-(CH-HDL)-TG/5 where CH is the total cholesterol concentration, (CH-LDL) is the cholesterol LDL concentration, (CH-HDL) is the RDL concentration and TG is the triglyceride concession (including free glycerol).

The HDL, CH and TG concentrations must be determined before the LDL concentration can be calculated and it will be appreciated that any errors in the measurement of the HDL, CH and TG concentrations will be compounded in the calculation of the LDL concentration. In addition, the conventional measurement of TG concentration does not discriminate between triglycerides and free glycerol, concentrations which can vary introducing a further error into the calculation of the LDL concentration. Thus, the calculation of LDL concentration inherently includes errors which can be extremely significant, particularly at high triglyceride levels. Such errors are a particular problem in, for instance, monitoring the progress of widely used LDL decreasing treatments (such as diets, medicine etc) in which it is necessary to accurately monitor relatively small decreases in LDL concentration (typically of the order of several percent) whilst triglyceride levels may be changing dramatically.

A further disadvantage of the conventional assay procedure described above is that whilst total CH and TG assays involve straightforward techniques performed on the whole plasma sample, the measurement of he HDL concentration requires a preliminary separation process in which the LDL and VLDL components are removed (by coagulating the LDL plus VDL and removing them by centrifuge).

A yet further disadvantage of the above method is that it provides no measurement of VLDL concentration which must therefore be determined from some different method or process, for instance by calculating the VLDL concentration on the basis of plasma triglyceride and free glycerol content estimated enzymatically.

An alternative method for assaying the total lipoprotein concentration of blood plasma, which is mainly the sum of LDL plus VLDL, is disclosed in two Russian patents, numbers SU1457386 and SU1476384. These relate to the use of a particular organic luminophore, 4-dimethylamino-4'-difluoromethyl-sulphonyl-benzylidene-acetophenone (DMSBA), as a florescent probe. The formula of the probe, identified as K-37, is given below:

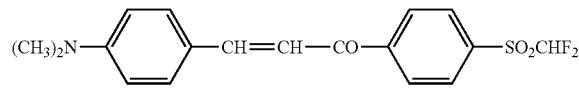

The probe K-37 is not luminous in water but is highly luminous in aqueous protein solutions such as blood plasma. In particular, the intensity of the florescence is highly dependent upon the lipoprotein content of the blood plasma and thus K-37 can be used as a probe to discriminate between lipoprotein concentration and the concentration of other proteins that may be present.

Russian patent number SU1457386 describes a method for synthesising K-37 and Russian patent number SU1476384 describes a method of calculating the total CH and TG content of blood plasma from a measurement of the steady state fluorescence of a mixture of a sample of blood plasma and K-37 (with reference to the measured florescence and known concentration of a standard sample). A blood sample to be assayed is diluted using a buffer solution (pH7.4, containing 10 mN Tris-HCL and 2 mN EDTA) and then centrifuged to remove red blood cells and other formed elements. A small amount (10 μl) of a 1 mN standard solution of K-37 is then added to 1 ml of the supernatant solution and the intensity of the resultant florescence is measured using a florescent spectrophotometer, at excitation and observation wavelengths of 440 nm and 550 nm respectively. A formula is disclosed for calculating the overall concentration of CH and TG from the measured florescence of the sample to be assayed and the measured florescence of K-37 in a standard sample of plasma with a known CH and TG concentration at a known dilution. Results for the repetition of the process for a number of different dilutions of the sample to be assayed from 50 fold to 500 fold dilution establishes that the determination of the total concentration of CH and TG is largely independent of the blood dilution.

Thus, use of K-37 as a florescent probe provides a very sensitive assay procedure, so that only very small plasma samples are required, which is relatively simple to perform requiring no separation of protein components. The concentration of CH and TG determined in this way can then be used as a direct indication of hyperlipidemia by comparing the calculated results with normal values.

One shortcoming of the above method is that it does not discriminate between the different classifications of lipoprotein and thus cannot, for instance, be used to monitor small changes in LDL concentration.

It is an object of the present invention to obviate or mitigate the above disadvantages.

SUMMARY OF THE INVENTION

According to the present invention there is provided a method of assaying to determine the identity and/or concentration or relative concentration in a sample solution of a particular one of a number of different target molecule types, the method comprising the steps of:

i) adding to the sample a probe substance which binds to the or each target molecule type and which when so bound fluoresces under appropriate excitation;

ii) performing a time-resolved fluorescence measurement on the sample; and iii) making said determination from analysis of the time decay data obtained from said time-resolved fluorescence measurement.

DETAILED DESCRIPTION

The present invention is based on the recognition that a single probe which binds to each one of a range of target molecule types can give information on the identity and/or concentration (or relative concentration) of the particular target molecule types present in the sample solution by reference to the fluorescence decay lifetime.

Preferably the probe substance is selected to have a different and characteristic fluorescence intensity decay as a function of time for each one of said target molecule types.

The present invention involves a true florescence lifetime measurement as distinct, for instance, from time-gated measurement systems which typically have an electronic time window open to receive florescence lifetime events between two points in time on the sub-nanosecond and nanosecond time scales. As such, time-gated measurement methods do not directly measure the lifetime. Examples of known fluorescence lifetime measurement methods which may be used in the present invention are the pulse coincidence, phase shift or modulation methods (the latter two either by single or multiple frequency excitation.

Analysis of the data obtained from the time-resolved fluorescence measurement could be performed in a number of ways. The preferred method is to identify a parameter which represents the decay lifetime, which may well be an exponential time constant derived as a result of a multi-exponential analysis performed on the time-resolved fluorescence measurement data.

In single-component sample solutions, i.e. samples containing only one of the range of the target molecule types with which the probe substance binds, the particular target molecule type present can be identified immediately from the time-resolved fluorescence measurement data. This identification can be made without requiring any further measurement.

Where the sample solution contains two or more of said target molecule types the present invention can be used to determine the concentration of a particular selected one of said target molecule types as a fraction of all target molecule types present. Again, no additional measurement is required to obtain this information.

The present invention is particularly suitable for determining the concentration of particular classes of lipoproteins present in protein mixtures such as blood serum or plasma. In this case, the probe substance is preferably K-37 identified above.

Figure 1:
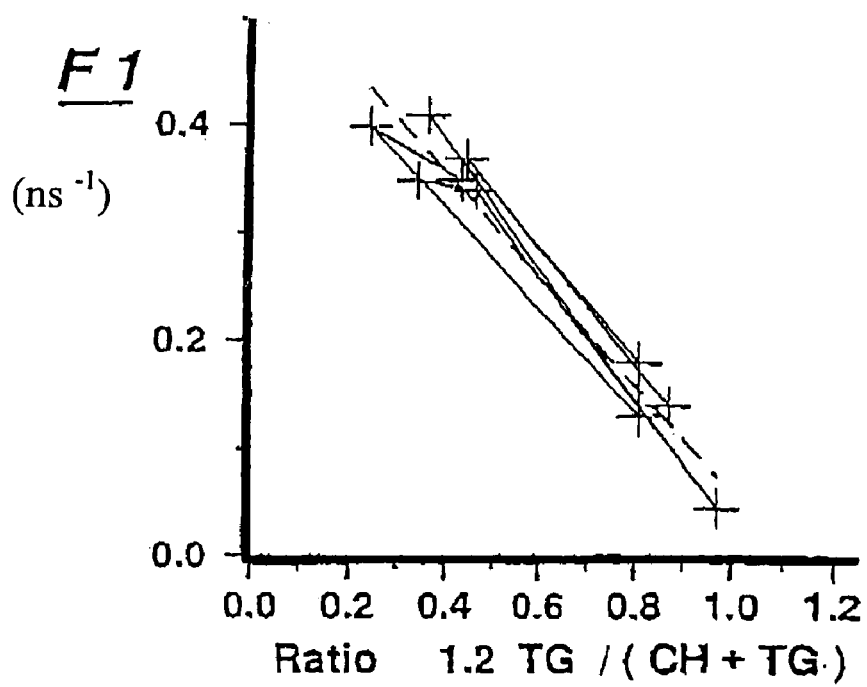
FIG. 1 is a graph showing the relationship of the fluorescent parameter F1 to the ratio of VLDL: total lipoprotein, as described in Example 2.

Examples of operation of the present invention will now be described, with reference to the accompanying figures, in which:

FIG. 1 is a plot referred to in relation to example 2 below; and

Figure 2:
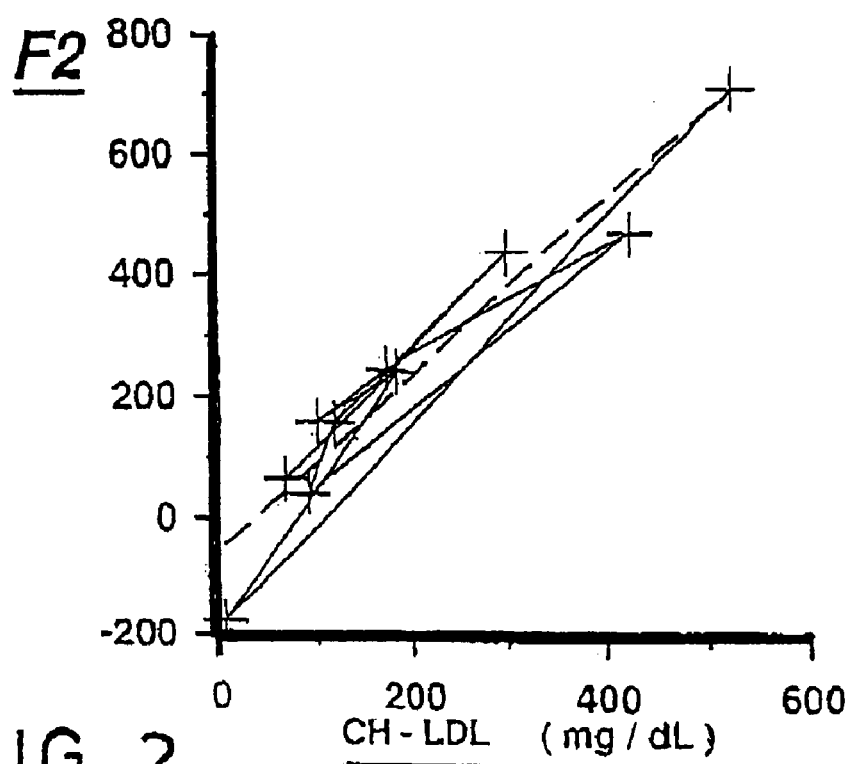
FIG. 2 is a graph showing the relationship of the fluorescent perameter F2 to LDL cholesterol, as described in Example 3.
Figure 3:
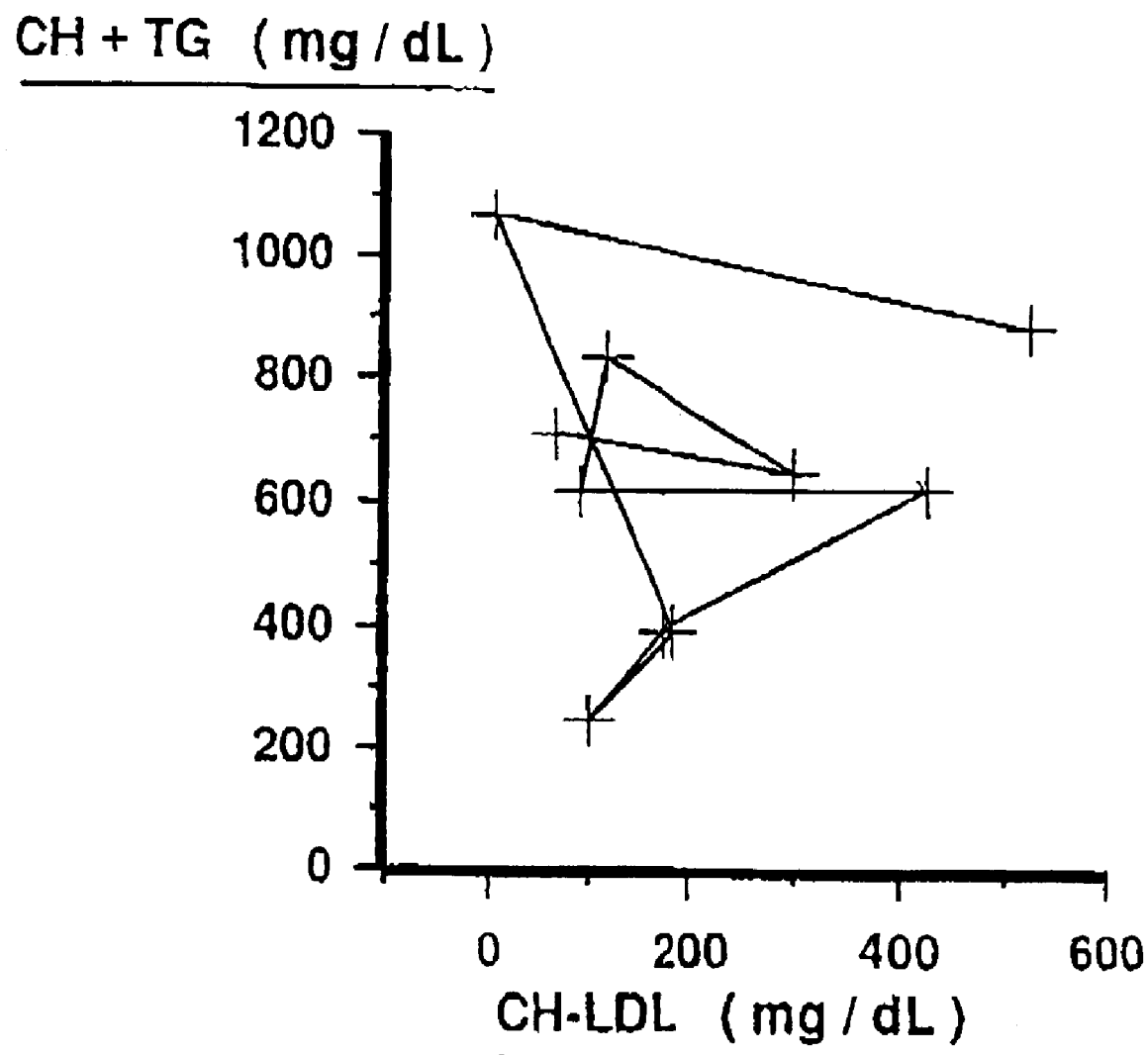
FIG. 3 is graph showing the relationship of tatal lipoprotien (total cholesterol plus total triglycerides) to LDL cholesterol.

FIGS. 2 and 3 are plots referred to in relation to example 3 below.

As mentioned above, the present invention is based on time-resolved fluorescence measurements using a fluorescent probe (K-37) which fluoresces when bound to the lipids of lipoproteins and excited at appropriate radiation wavelengths. The basic principles of time-resolved fluorescence measurements are well known and involve illuminating a sample with periodic short pulses of radiation at a particular wave length (or over a particular range of wave lengths) and measuring the decay in the intensity of fluorescence over time following each pulse. In the experiments described below a synchrotron source has been used to excite the samples and the single photon counting method has been used to derive the time decay data. There are many published references relating to such fluorescence lifetime measurements including: Munro I. H., (1980), "Synchrotron radiation as a modulated source for fluorescence lifetime measurements and for time resolved spectroscopy"; chapter 8 of Synchrotron Radiation Research Eds., Winick H, Doniachs, Plenum Press New York; Munro I. H, Schwenter N, (1983) "To Time Resolved Spectroscopy using Synchrotron Radiation" Nuclear Instruments and Methods, 208,819; and O'Connor, D. V. Philips Hillips. D. (1984) Time-Correlated Single-Photon-Counting, Academic Press, London. It will, however, be understood that any technique suitable for the measurement of fluorescence lifetimes, may be used.

EXAMPLE 1

Lipoprotein Discrimination and Lipoprotein Type Identification in Single-Component Solutions Human serum lipoproteins VLDL and LDL were obtained from donor sera by a process of ultracentrifugation using well established conventional methods. Respective aqueous solutions of each sample were then prepared, each lipoprotein having a concentration of 1 g/L in 0.14M NaCl, 0.01M tris-HCl pH 7.3. The probe K-37 was then slowly added under stirring to each sample solution.

Each sample was then subjected to a time-resolved fluorescence measurement in accordance with the present invention using the synchrotron source at the Daresbury Laboratory (Daresbury, Warrington, Cheshire, England) at an excitation wavelength of 440 mn, The single photon counting technique was then used to collect time-resolved decay data of photons equivalent in energy to the detection wavelength of 550 nm. A multi-exponential analysis of the results was then performed using the non-linear least-squares method to represent the time dependence of the intensity decay as a series of exponentials of decreasing amplitude, i.e.:

$$F(t)=A_1\times\exp(-t/\tau_1)+A_2\times\exp(-t/\tau_2)+$$

where $A_1, A_2 \ldots A_n$ are amplitudes and $\tau_1, \tau_2, \ldots \tau_n$ are respective decay time constants.

The above mathematical analysis reveals that $\tau_1=3.1$ nanoseconds for the VLDL solution and $\tau_1=4.1$ nanoseconds for the LDL solution. The error in the calculation of these values is only of the order of 0.2 nanoseconds so that the difference between the two values is clearly significant. Accordingly, measurement of $\tau_1$ for any particular single-component solution containing either LDL or VLDL will reveal which lipoprotein is present. In other words, performance of the time-resolved fluorescence measurement in accordance with the present invention using the K-37 probe discriminates between VLDL and LDL and the measurement of $\tau_1$ can be assumed as a parameter for identification of VLDL or LDL in respective solutions.

The example demonstrates that the time-resolved fluorescence decay of lipoproteins is highly dependent on the density of the lipoprotein. Although only LDL and VLDL solutions have been used, the example can be repeated with other lipoprotein classes, such as HDL, to establish their particular characteristic decay time-constants.

EXAMPLE 2

Determination of the VLDL Fraction in a Lipoprotein Mixture (Blood Serum)

Given that different lipoproteins have different fluorescence decay time-constants as measured using K-37, this example shows how measurement of the time-resolved fluorescence decay of a lipoprotein mixture can be used to give direct information as to the relative concentrations of the different lipoproteins present in that mixture.

Ten blood serum samples were taken from different donors selected to have wide variations in cholesterol (CH) and tryglyceride (TG) content and determination of lipid concentration was then made on a portion of each sample using routine enzymatic analysis in a clinical autoanaylser. Such techniques are conventional. This gave three values for each sample, namely the total CH concentration, the total TG concentration and the HDL cholesterol (CH-HDL) concentration The biochemically measured values are given in table 1 set out below.

TABLE 1

| Serum No | Total CH mg/dL | Total CH mg/dL | CH-HDL mg/dL |
|---|---|---|---|
| 1 | 197 | 513 | 27 |
| 2 | 410 | 239 | 63 |
| 3 | 271 | 566 | 41 |
| 4 | 201 | 416 | 27 |
| 5 | 499 | 124 | 49 |
| 6 | 252 | 142 | 51 |
| 7 | 178 | 71 | 64 |
| 8 | 244 | 150 | 31 |
| 9 | 201 | 867 | 22 |
| 10 | 623 | 266 | 45 |

It will be seen from table 1 that the CH and TG levels vary widely across the samples up to very high values of 623 mg/dL and 867 mg/dL respectively. Moreover, the CH:TG ratio varies from 0.23 to 4.0, i.e. by seventeen times. The range of these variations encompasses more than 98% of the values that can be expected to be found in a typical European population.

A time resolved decay measurement was then performed on each sample, the samples being prepared, and the fluorescent measurement being performed, as described above in relation to example 1. The measured values of the decay times, $\tau_1$, are given in table 2 below.

TABLE 2

| Serum No | Decay time $T_1$ ns |
|---|---|
| 1 | 3.17 |
| 2 | 3.71 |
| 3 | 3.25 |
| 4 | 3.15 |
| 5 | 3.8 |
| 6 | 3.66 |
| 7 | 3.67 |
| 8 | 3.65 |
| 9 | 2.98 |
| 10 | 3.85 |

Given that it is well known that human blood serum triglycerides originate mainly from VLDL and total CH originates from all lipoproteins, and that VLDL cholesterol concentration is about 0.2 of the VLDL triglyceride concentration, the ratio of VLDL: total lipoprotein concentration can be represented by the following expression:

(CH-VLDL+total TG)/(total CH+total TG)=1.2 (total TG)/(total CH+total TG)

Analysis of the measured decay times by reference to the biochemically determined data establishes that $\tau_1$ of the mixture is closely related to the relative concentrations of lipoproteins present within that mixture. The close correlation between the VLDL fraction of the total lipoprotein concentration of the sample and the measured time-constant $\tau_1$ can be illustrated using the following fluorescent parameter F1:

$$F1=2.0-(6.2/\tau_1)$$

A plot of the VLDL fraction (as represented above and calculated using the biochemical derived data of table 1) against the fluorescent parameter F1 (calculated from the measurement $\tau_1$ given in table 2) is shown as FIG. 1. This shows that there is a very tight linear correlation between the two. The co-efficient of the linear correlation is r=−0.98 (i.e. very close to 1).

Thus, knowing the correlation between $\tau_1$ and the VLDL fraction established above, the VLDL fraction of the total cholesterol content of any blood serum sample can be derived using the present invention on the basis of a single measurement, i.e. the time constant $\tau_1$. No other measurement, and no prior separation of the blood serum cholesterol components, is required.

Whilst the above example establishes the relationship between $\tau_1$ and the VLDL fraction, similar relationships can be established between $\tau_1$ and the fractional concentrations of other lipoproteins including VDL and HDL.

EXAMPLE 3

Determination of LDL Concentration in Blood Serum

Since the fractional concentration of any particular class of lipoprotein relative to the total lipoprotein concentration can be found from $\tau_1$ (as established by example 2 above), it follows that the absolute concentration can be calculated from a separate measurement of the total CH+TG concentration.

As mentioned in the introduction to this specification it is very important to be able to accurately measure the LDL concentration in blood serum. This example illustrates how the present invention may be used to greatly simplify measurement of LDL concentrations.

Using the biochemical data of table 1, and the related time-decay measurements of table 2, FIG. 2 is a plot of LDL cholesterol (CH-LDL) against a fluorescent parameter F2, set out below:

$$F2 = (CH+TG) \times [1.8 - (5.6/\tau_1)]$$

FIG. 2 shows that there is a very close correlation between the fluorescent parameter F2 (and thus $\tau_1$) and the LDL concentration over the wide range of concentrations exemplified by the samples used. The co-efficient of linear correlation is r=0.96. Thus, the present invention provides a method for determining the LDL concentration in blood serum requiring only two measurements, namely $\tau_1$ and the total CH+TG which can be readily obtained using well known and relatively simple clinical techniques. The LDL determination according to the present invention is therefore much simpler and straight forward to perform than that of the prior art.

It should be noted that the correlation between the parameter F2 and the VDL concentration cannot be attributed to the use of biochemically derived data, namely CH+TG, in the calculation of parameter F2. The value CH+TG does not in fact have any significant correlation with the CH-LDL concentration as is, shown in FIG. 3 which plots one against the other. In the case of FIG. 3 the co-efficient of linear correlation is very close to zero (r=0.06).

Results obtained from the present method show no significant randum errors. It is therefore possible to assume that any small errors are systematic in character and dependent on the particular patient etc from which the sample is taken and therefore will be present in all tests on that patent and thus will have no effect on the ability to accurately monitor small changes in, for instance, LDL levels over time.

As mentioned in the introduction to this specification, the intensity of fluorescence of K-37 does not appear to be dependent upon the extent of dilution of the blood serum and thus the preset invention has grew sensitivity requiring only small samples to be taken from a patient etc. In addition, the results obtained are consistent and reproducible which is particularly important in measuring changes over long treatment cycles.

It will be appreciated that obtaining the time-resolved fluorescence data is a single step operation, requiring no prior separation of the serum lipoproteins. In addition, the fluorescence lifetime results can be obtained within one minuet of the addition of the probe K-37.

It will be appreciated that the present invention may be performed to identify lipoprotein content of protein mixtures other than blood serum and plasma.

The invention claimed is:

1. A method of assaying to determine identity and/or the concentration or relative concentration of a particular class of lipoprotein in a sample solution containing a mixture of at least two different classes of lipoproteins, the method comprising the steps of:
    i) adding to the sample a probe substance which binds to each class of lipoprotein and which when so bound fluoresces under appropriate excitation, wherein said probe substance is K-37;
    ii) performing a time-resolved fluorescence measurement on the sample, the probe substance having a different and characteristic fluorescence intensity decay as a function of time for each one of said different classes of lipoprotein; and
    iii) determining the identity and/or concentration or relative concentration of a particular class of lipoprotein from analysis of the fluorescence decay data obtained from said time-resolved fluorescence measurement.

2. A method according to claim 1, wherein said determining step (iii) is made from a parameter indicative of the time-resolved intensity decay representative of the rate of decay.

3. A method according to claim 2, wherein said analysis of step (iii) includes a multi-exponential analysis of the time-resolved fluorescence measurement data to determine a decay time-constant, said determination being made as a function of said time-constant.

4. A method according to claim 3, wherein said multi-exponential analysis represents the time-resolved fluorescence decay as a function of a series of exponentials of decreasing amplitude and said time constant is the time-constant of the most significant of the exponentials.

5. A method according to claim 1, wherein step (iii) comprises determining the concentration of a first lipoprotein class relative to the total lipoprotein concentration including all classes of lipoprotein present in the sample.

6. A method according to claim 1, wherein step (iii) comprises determining the concentration of a lipoprotein class from the combination of said time-resolve decay measurement data and a separate measurement of total lipoprotein concentration including all classes of lipoprotein present in the sample.

7. A method according to claim 5, wherein said total lipoprotein concentration including all classes of lipoprotein present in the sample includes different densities of lipoprotein.

8. A method according to claim 5, wherein said lipoprotein classes are HDL, LDL and VLDL.

9. A method according to claim 1, wherein said sample is obtained from blood serum or plasma.

10. A method according to claim 6, wherein said separate measurement of the total lipoprotein concentration is obtained biochemically.

* * * * *